US006189394B1

United States Patent
Sullivan et al.

(10) Patent No.: US 6,189,394 B1
(45) Date of Patent: Feb. 20, 2001

(54) ON-LINE POWER SLIDING DOOR TEST METHOD

(75) Inventors: Brian Kenneth Sullivan, Plymouth; Robert Edward Kosior, Livonia; Grace Ann Chamberlain, Clarkston, all of MI (US)

(73) Assignee: Ford Global Technologies, Inc., Dearborn, MI (US)

( * ) Notice: Under 35 U.S.C. 154(b), the term of this patent shall be extended for 0 days.

(21) Appl. No.: 09/347,886

(22) Filed: Jul. 6, 1999

(51) Int. Cl.[7] .................................................... G01N 19/00
(52) U.S. Cl. ................................ 73/865.9; 49/166; 70/95
(58) Field of Search ........................ 73/862.381, 862.01, 73/862.57, 865.9; 49/166; 70/95

(56) References Cited

U.S. PATENT DOCUMENTS

| 2,833,348 | | 5/1958 | Almquist. | |
|---|---|---|---|---|
| 4,842,313 | | 6/1989 | Boyko et al. . | |
| 4,866,881 | * | 9/1989 | Morrow et al. | 49/25 |
| 4,894,952 | * | 1/1990 | Trett et al. | 49/25 |
| 5,142,152 | * | 8/1992 | Boiucaner | 250/341.7 |
| 5,189,839 | * | 3/1993 | DeLand et al. | 49/360 |
| 5,641,918 | | 6/1997 | Odenwald . | |
| 5,708,338 | * | 1/1998 | Cook et al. | 318/466 |

* cited by examiner

*Primary Examiner*—Max Noori

(57) ABSTRACT

An in-line testing method for non-intrusively testing the force required to complete the closure of a power assisted sliding door assembly onto a door opening having resistance seals, comprising: (a) providing a door switch and a timing device within the power assist sliding door assembly to at least measure the time lapse from a door ajar position to a door locked position; and (b) if the time lapse is slower than a pattern time lapse for a model assembly of the same door known to be properly fitted, adjusting the door ajar gap in the test assembly to reduce the force required to achieve a door locked position.

6 Claims, 6 Drawing Sheets

PROVIDE SENSOR AND TIMING DEVICE FOR POWER-ASSIST SLIDING-DOOR ASSEMBLY TO MEASURE TIME LAPSE FROM DOOR AJAR POSITION TO DOOR LOCKED POSITION

ADJUST DOOR AJAR GAP IN THE ASSEMBLY IF TIME LAPSE IS SLOWER THAN A PATTERN TIMING LAPSE FOR A MODEL SLIDING DOOR ASSEMBLY THAT IS PROPERLY FITTED

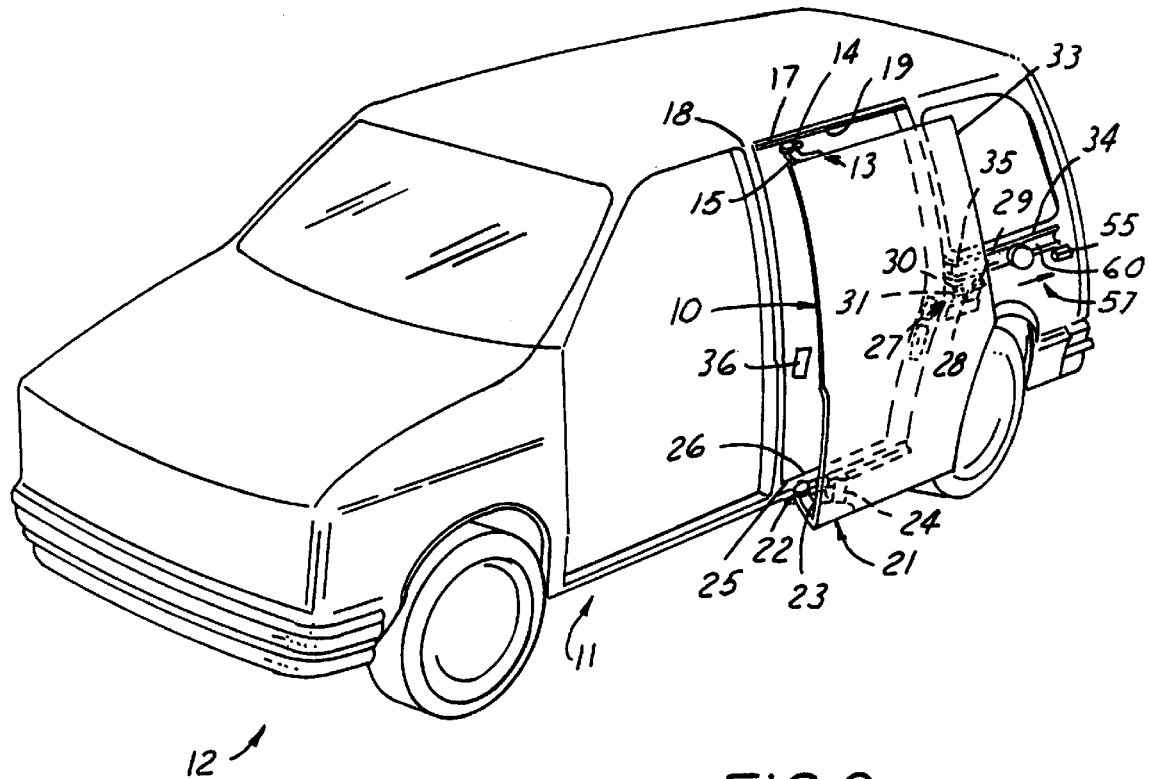

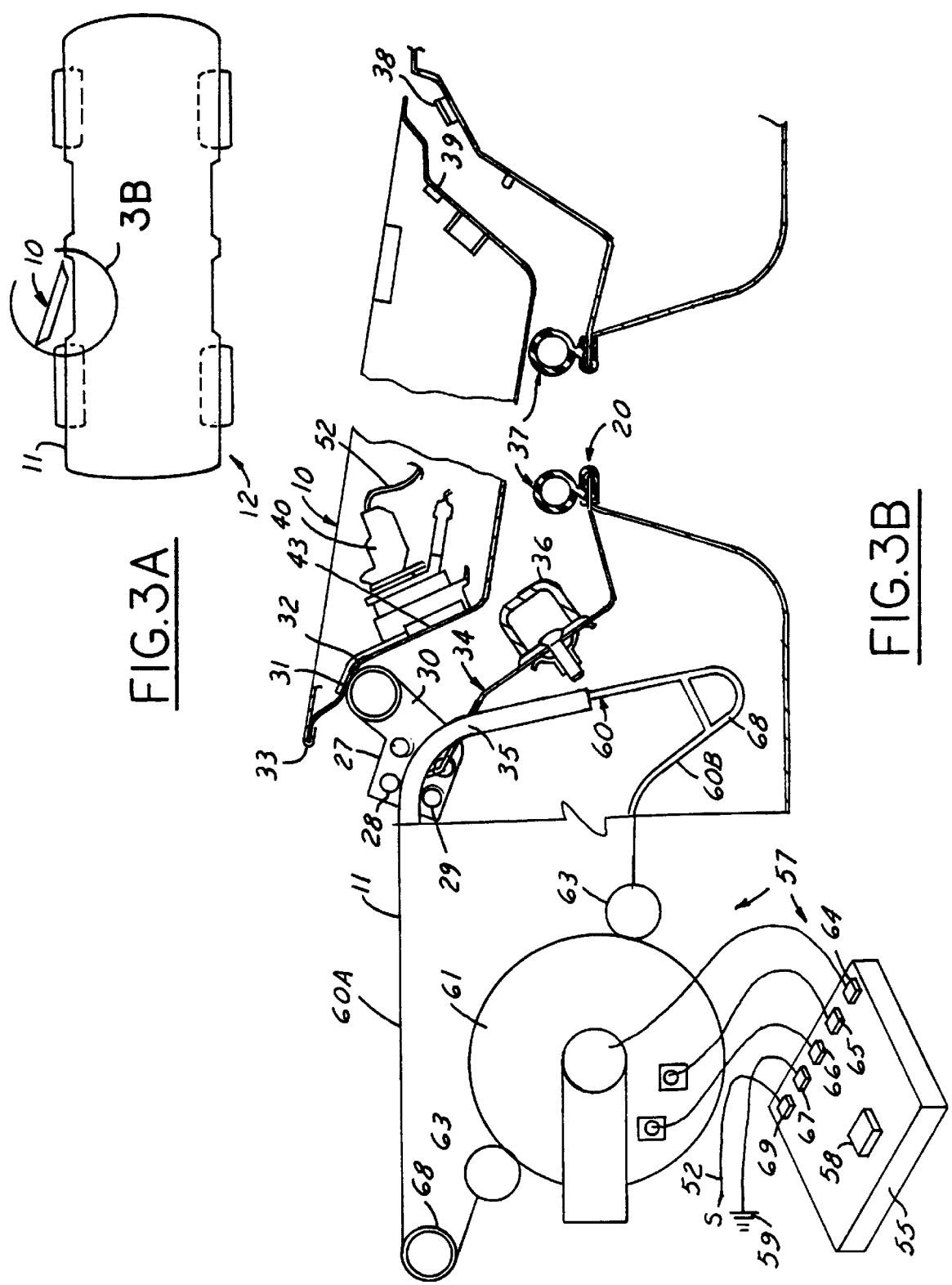

ON-LINE POWER SLIDING DOOR TEST METHOD

TECHNICAL FIELD

This invention relates to the technology of detecting vehicular fitting defects and more particularly to detecting very slight defects in a close tolerance power-assisted door closure system while doing so in a non-intrusive on-line manner that allows for essentially 100% discovery of defect instances, and which method promotes adjustments to the power sliding door system so that it will function properly for the life of the vehicle.

DISCUSSION OF THE PRIOR ART

Automotive vehicle closure members that are slidingly mounted, such as sliding side doors on minivans, typically require only small forces to move them through the major extent of their opening and closing movement relative to the vehicle body. It is only during the final closing movement of the closure member, at which time the closure member must compress weather seal strips carried by the vehicle body that a large application of force must be applied to the closure member. To overcome the resistance encountered in the final closing moments, a power assist unit is used which may comprise an electric motor powered by the battery of the vehicle; the motor pulls different cables to either close or open the sliding door. Such power unit has its most critical function when the door has reached what is known as a latch initiation stage (secondary latch position) where a latch bolt, movable between latched and unlatched positions, is engaged by the door catch at the latch initiation stage. From this point in time to the final compression of the door seals achieving complete door closure (primary latched position) the maximum designed force of the power unit is applied. Such time lapse is hereinafter referred to a s/p time (secondary/primary).

Although non-automated or manual methods are available for off-line testing, applicant is unaware of any automated or on-line test procedure for accurately verifying the fitting of automotive closure members within very close tolerances.

SUMMARY OF THE INVENTION

The invention is a method of testing for automotive power assisted sliding door closure defects with: (i) the door having hinge slides received in tracks for carrying the door across and toward a door opening in an automotive body, (ii) the door opening having a bolt or catch for locking with a latch on the door and having resilient seals arranged around the opening which must be compressed during closure, and (iii) the door movement being selectively powered by a power unit connected to the door through cables to move the door from a fully opened condition to a latch locking initiation stage which provided a predetermined door ajar gap, to a completed latch locked stage accompanied by full door closure. The method comprises the steps of: (a) providing a sensor and timing device within the power unit to at least measure the S/P time experienced between the latch locking initiation stage and the completed latch lock stage; b) comparing the S/P time lapse for a power sliding door assembly being tested to the pattern S/P time lapse for a power sliding door known to be properly fitted; and c) if the test S/P time lapse is slower than the pattern S/P time lapse for the same door assembly, adjusting the latch or closure wedges to change the door ajar gap for reducing the force required by the power unit to close the door.

In another aspect, the invention is an in-line method of non-intrusively testing the force required to complete the closure of power assisted sliding door assembly onto a door opening having resistance seals, comprising: (a) providing a sensor and timing device within the power assist sliding door assembly to at least measure the time lapse from a door ajar position to a door locked position; and (b) if the time lapse is slower than a pattern time lapse for a model assembly of the same door known to be properly fitted, adjusting the door ajar gap in the test assembly to reduce the force required to achieve a door locked position.

BRIEF DESCRIPTION OF THE DRAWINGS

FIG. 1 is a block diagram of the essential steps of the method improvement of this invention;

FIG. 2 is a perspective view of a vehicle having a power sliding door assembly ready for an in-line non-intrusive test according to the method of this invention to detect fit defects and accompanying excessive closing forces (the door being shown in a semi-open position);

FIG. 3A is a schematic plan view of a vehicle showing a sliding door assembly that is to be tested according to this invention;

FIG. 3B is an enlarged view of a portion of FIG. 3A showing the power controls associated with the sliding door assembly;

DETAILED DESCRIPTION AND BEST MODE

Figure 4:
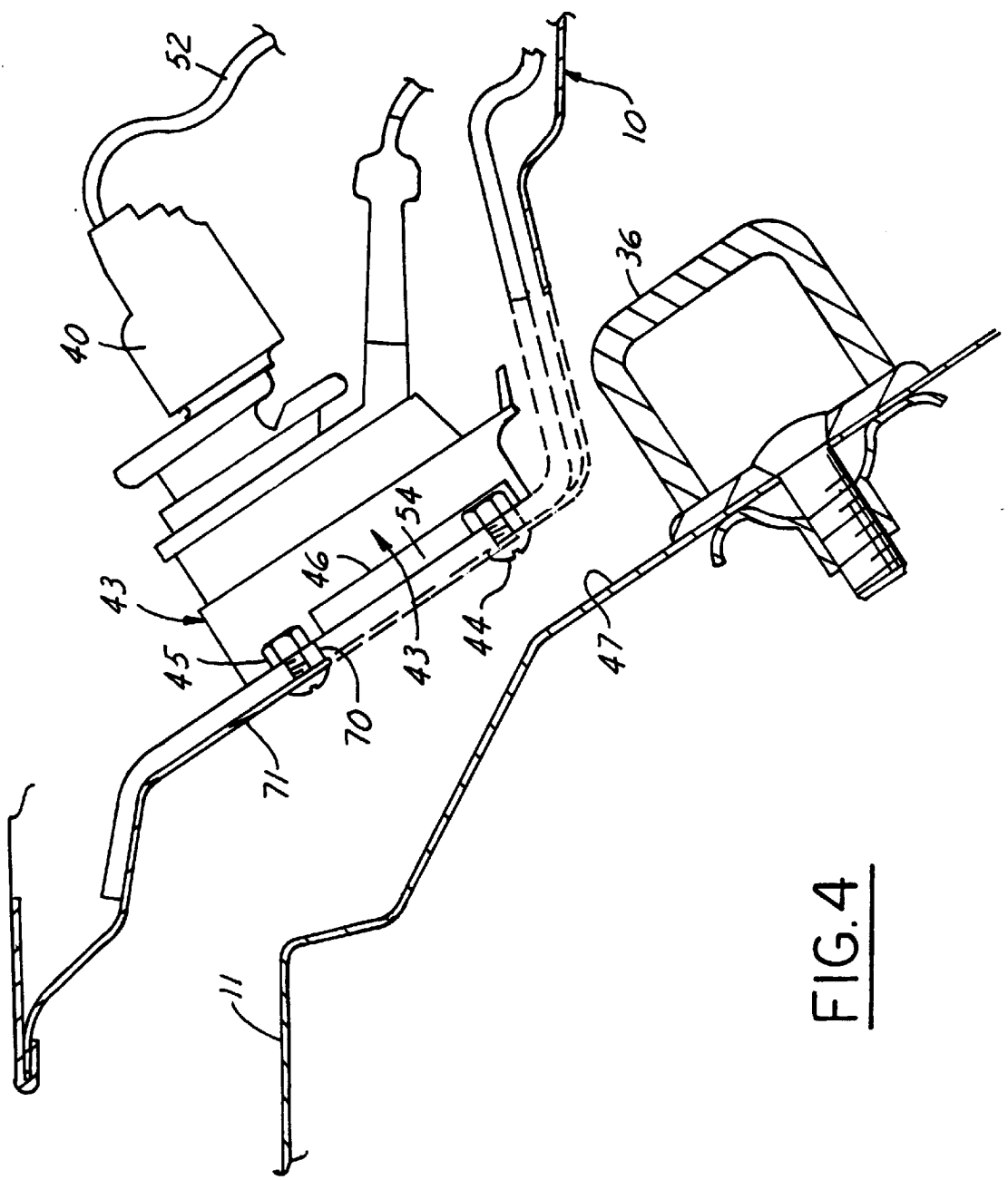
FIGS. 4, 5 and 6 are enlarged sectional views of a portion of the sliding door assembly showing the door respectively in (i) the fully unlatched position; (ii) a secondary latch initiation position, or door ajar, and (iii) a locked door, or primary latched position.

As shown in FIGS. 2, 3A and 3B, an automotive sliding door 10 is supported on an auto body 11 of an automotive van 12 at three locations. A first point of support comprises a slider 13 with an upper roller 14 carried by an arm 15 that is fastened to the door 10 at an inside horizontal ledge 16. The roller 14 engages an upper guide rail 17 that is attached to the upper portion 18 of the vehicle body 11 as shown and extends along the extent of the upper edge 19 of the door opening 20. A second point of support is a slider 21 with a lower roller 22 carried by the arm 23 fastened to a lower upright inside panel 24 of the door 10. The roller 22 rides in a lower track 25 as shown. The lower track extends along the extent of the lower edge 26 of the door opening 20.

As shown in FIG. 3, the third point of support is a mid-level slider hinge 27 having a pair of rollers 28, 29 carried by an arm 30 that is journalled to a bracket 31 fastened to an inside mid-level panel 32 (located at the trailing edge 33 of the door 10). The pair of rollers 28, 29 engage a mid-level track 34 that extends rearwardly from the door opening 20. The entrance portion 35 of the track 34 is curved inwardly from the side plane of body 11 to move the door against the flexible door seals 37 and create a sealed closure.

It is difficult to visually observe when the alignment of a door is unable to achieve a secure and locked closure with minimum effort. It takes good alignment between a latch 43 and a striker 36; both are mounted on sheet metal respectively (the latch 43 on the door 10 and the striker 36, on the vehicle body 11), which sheet metal can vary slightly in crown shape and form, thereby causing the latch 43 and striker 36, as well as door wedges 38 and receptors 39, to mismatch by as much as 10 mm. (typically by about 5 mm). Thus, problems related to wrong fitting closure elements may not be detected during assembly and, if observed, heretofore had to be remedied off-line by trial and error.

Figure 5:
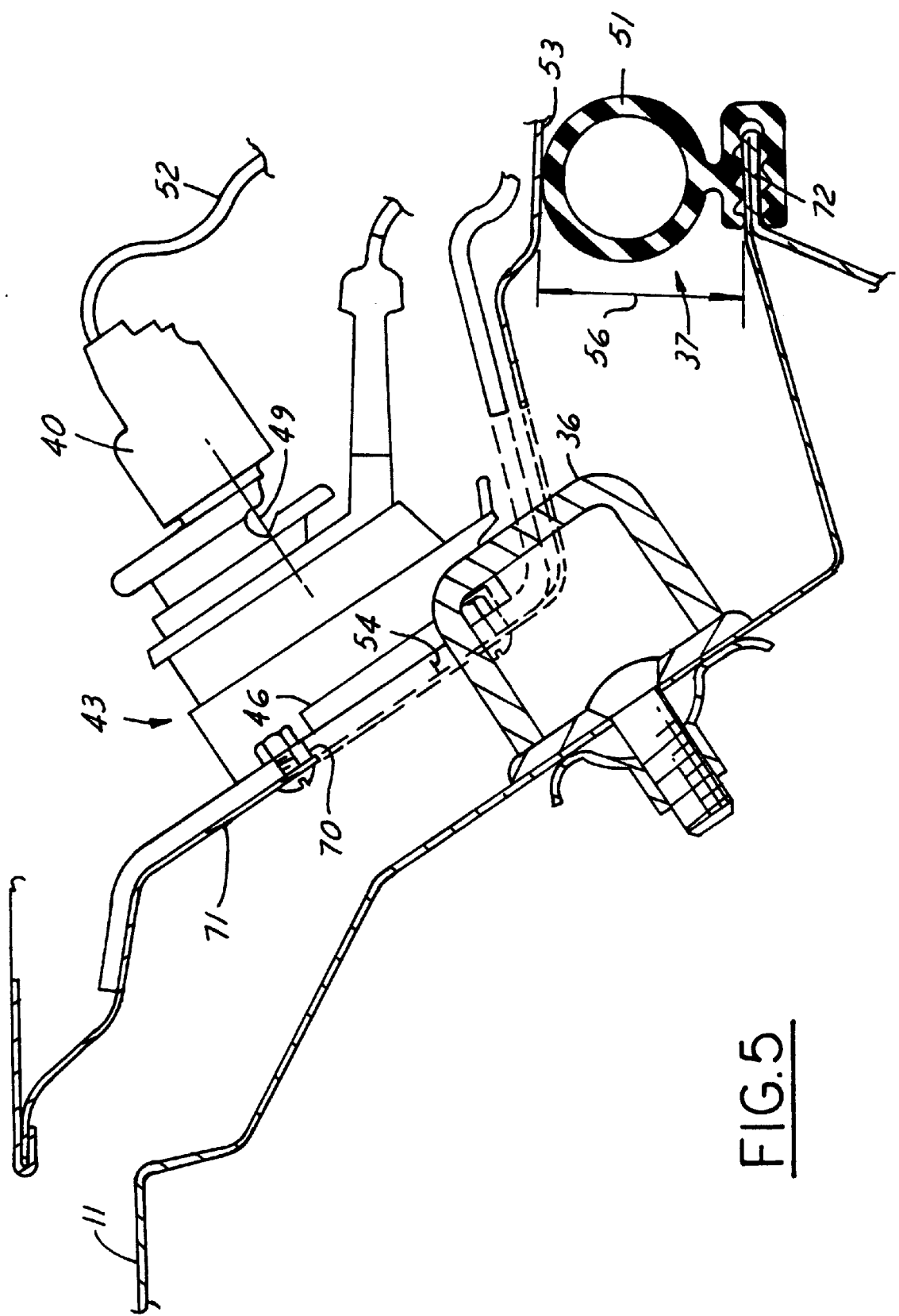
Figure 6:
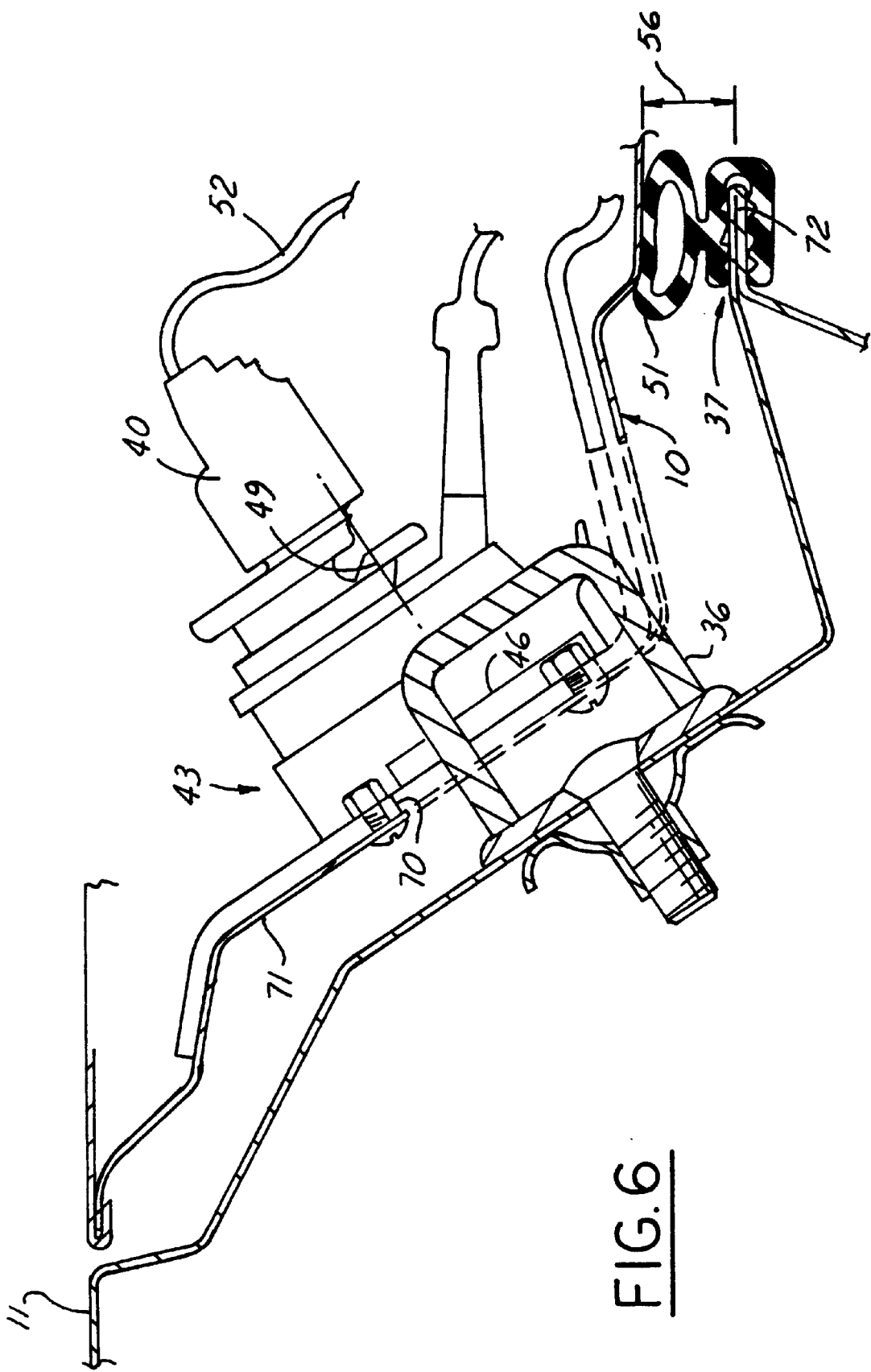

The method of this invention efficiently overcomes such handicaps. It has been discovered that the variance in force required to bring about complete closure of a powered sliding door is directly proportional to the variance in time needed to achieve such. The method herein has found that if a door mounted switch 40 (operatively connected to the latch 43) is used to send a signal via wire 52 to an accurate microprocessor 58 of a control unit 57; such signal can be used to measure elapsed time from (i) the moment the power sliding door attains a door ajar (or latch initiation position 41, as shown in FIG. 5) to the moment (ii) it attains final fully locked closure position 42 (as shown in FIG. 6), such time lapse being measured in milliseconds. Such time lapse will be an accurate indicator of the relative degree of closure force required. The degree of excessiveness of the s/p time will foretell what adjustments need to be made online. When such excessive closing forces go undetected at assembly, they may lead to obvious faulty closures as well as inability to lock the sliding door when the vehicle experiences reduced energy levels from the battery which may feed the power unit of the sliding door assembly with insufficient power.

The door slider hinges are pulled along the tracks by a power assist cable 60 that is wound in two directions by the power unit 57. The cable has two parts, one part 60A connected to trailing side of hinge 27 and wound around drum 61 in one direction; the other part 60B is connected to the leading side of hinge 27 and is wound around drum 61 in an opposite direction. Thus, the drum can be rotated in either direction to either pull or push the door along its tracks. Tensioners 63 may be used to keep the cable parts taut as they travel around pulleys 68. The drum is selectively rotated by a motor 62 which is connected to the motor terminal 64 of the power unit which in turn receives power from a supply 59 through terminal 67. A travel sensor and a clutch within the drum assembly 61 are operatively connected to the control unit at respective terminals 65 and 66. The important aspect of the control unit 57 for purposes of this invention is that switch 40 is connected by wire 52 to it at terminal 69 so that a measurement of s/p time may take place.

As shown in FIG. 4, the latch mechanism 43 is supported on the door by screws 44 which extend through slots 45, allowing the mechanism to be shifted along the slots if the screws are loosened slightly. The latch mechanism 43 is adapted to cooperate with a striker 36 fixedly mounted on the inside wall 47 of the door opening 20. The latch mechanism 43 is adapted to receive the striker 36 through an opening 70 in wall 71 of the door. In the position of FIG. 4, the door is in the fully unlatched condition, with the latch mechanism spaced away from the striker 36. In FIG. 5, the power unit has pulled the door along the tracks so that its trailing edge is moving laterally toward the door opening. In the latch initiation stage of FIG. 5B, position 41, (door ajar) a plate latch 46 is not yet caused to rotate by engagement with striker 36 within its slot 54. This secondary or latch initiation stage (position 41) is attained when the door has been pulled by the cable 60 along the track 34 sufficiently to begin moving it laterally inwardly toward the hollow tubular portions of door seals 37, as guided by the curved portions 35 of the track. At this secondary stage, the following occurs: (i) the inner periphery 53 of the door may make touching contact with the tubular portions 51 of seals 37 in its expanded generally rounded condition, (ii) the spring biased plate latch 46 receives the striker or bolt 36 within its slot 54 while turning about its axis 49 in the "door ajar" condition, (iii) small wedges 38 on the door opening become Generally aligned with female wedge receptors 39 on the door, and (iv) a switch 40 connected to the control unit 55 of power unit 57, is tripped so that the microprocessor 58 can begin time lapse counting. The seal gap 56 between the body door frame at location 72 and the inner periphery 53 of the door should be about 23 mm. Fit between the door 10 and the door opening 20 may not be perfect at this stage due to one or more factors such as the latch mechanism 43 not fitting properly with the striker 36 due to the supporting sheet metal tolerances. As a result, the tubular portions 51 of seals 37 may be substantially crushed or overly stressed at this stage causing greater resistance to the door as it is moved further, or the wedges 38 may be slightly nonaligned with their receptor 39. These fit defects are usually very slight, no more than 1–3 mm.; but the resistance force, due to the misfit, is increased as the door continues the remainder of its closing operation.

Figure 7:
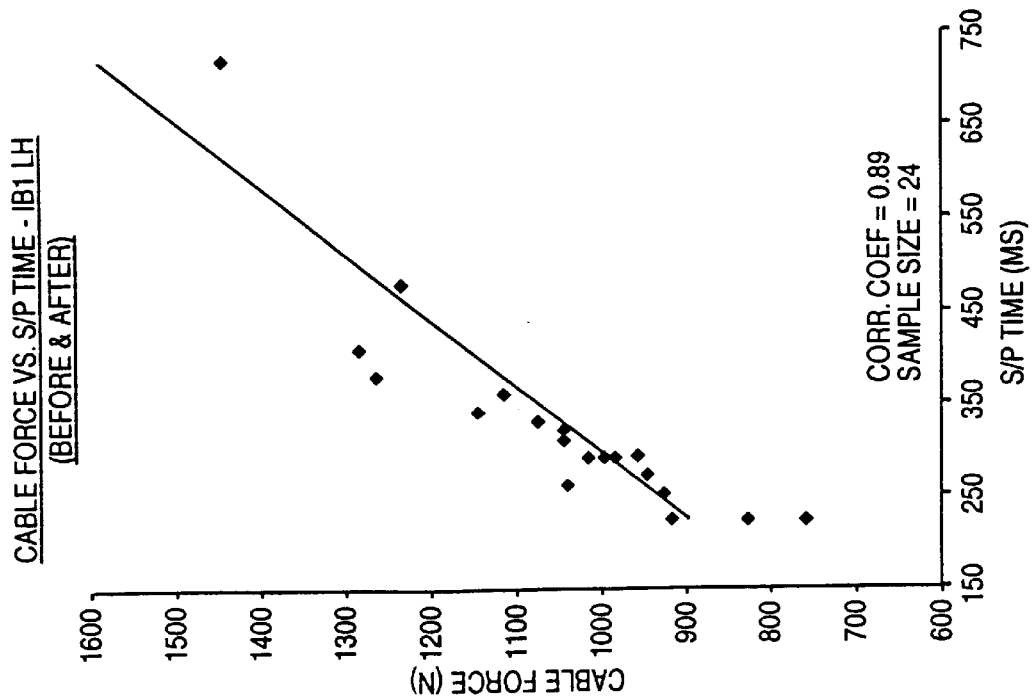

As the power unit 57 moves the door inwardly following the latch initiation stage, the tubular seals 51 are compressed and the plate latch 46 is further rotated by the striker 36 to a latch locking condition (primary latched condition). In the latch locked condition, the seal gap 56 has been reduced to about 13 mm. and the tubular portions 51 of seals 37 are compressed to a condition as shown in FIG. 7.

Figure 8:
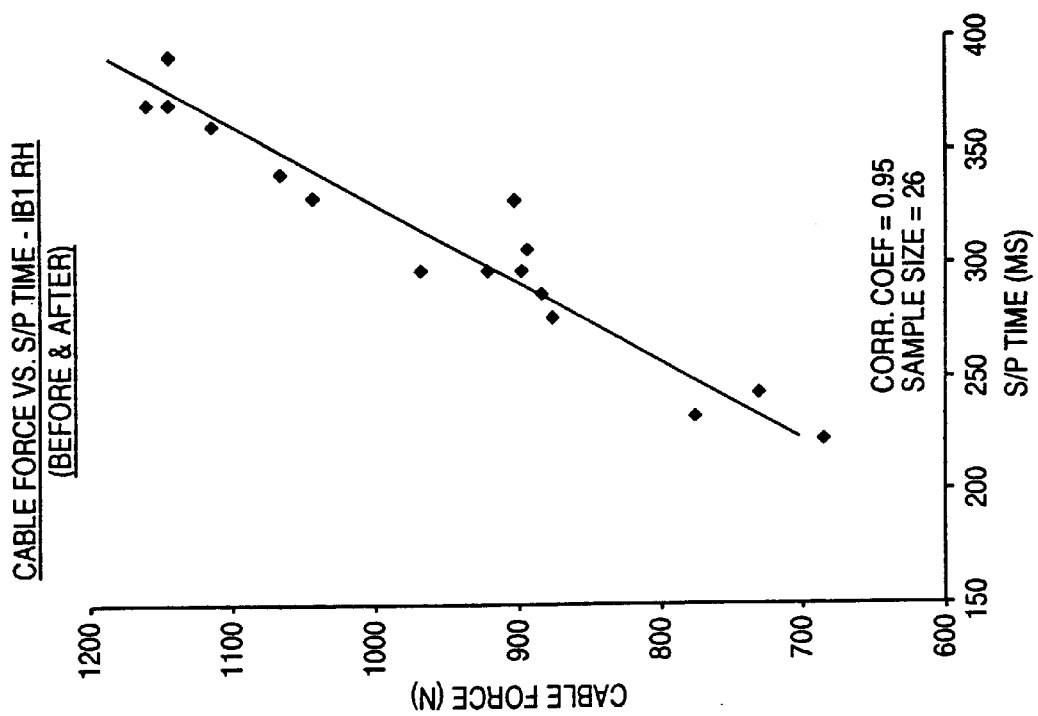
FIGS. 7 and 8 are graphical illustrations of calculated closure forces as a function of time between latch initiation and latch locking for several different door assemblies which have been tested on an assembly line before and after adjustment (FIG. 7 is for a left-hand door assembly and FIG. 8 is for a right-hand door assembly).

The time lapse from the latch initiation stage to the latch locked stage is proportionally affected by the amount of resistance encountered or lack of resistance. The time to latch is directly related to cable force. Excessive cable force leads to fatigue and a reduction in cable life cycle. FIGS. 7 and 8 show a plot of force as a function of s/p time. These graphical illustrations tell us that the door closing time (s/p time) is correlated to the cable force required to close the door.

While the invention has been shown and described in its preferred embodiments, it will be clear to those skilled in the arts to which it pertains that many changes and modifications may be made thereto without departing from the scope of the invention.

What is claimed is:

1. A method of testing for automotive power assisted sliding door closure defects, wherein i) the door has hinge slides received In tracks for carrying the door across and toward a door opening in an automotive body, ii) the door opening having a bolt for locking with a latch on the door and having resilient seals arranged around the opening which must be compressed during closure, and iii) the door movement being selectively powered by a power unit connected to the door through cables to thereby move the door from a fully opened condition to a latch initiation stage providing a predetermined door ajar gap and thence to a completely latch locked stage accompanied by full door closure with a door sealed gap, the improved method comprising:

a) providing a door switch and a timing device within the power unit triggered by such switch to at least measure the time lapsed between the latch initiation stage and latch locked stage;

b) comparing the time lapse for a power sliding door assembly being tested to the pattern time lapse for a power sliding door known to be properly fitted; and c) if the test time lapse is slower than the pattern time lapse for such door assembly, adjusting the latch or closure wedges to change the door ajar gap for reducing the force required by the power unit to compress said seals and close the door.

2. The method as in claim 1, in which said power assisted sliding door assembly is part of an automotive body assembly having other electrical controls, the method of testing being carried out and integrated with the test of all the electrical equipment for said body.

3. The method as in claim 1, in which said test carries out assessment of door closing force without directly measuring such force.

4. An on-line method of non-intrusive testing for the force required to complete closure movement of a power assisted sliding door assembly onto a door opening having resistance seals, said completion movement being between a secondary door ajar position and a primary door locked position, comprising:

(a) providing an attachable sensor device that signals and records the timing lapse of door movement between said secondary and primary movements of an assembly under test;

(b) using said sensor device to record such time lapse (i) for a test power assisted sliding door assembly unknown to be properly assembled, and (ii) for a reference power assisted sliding door assembly known to be properly assembled; and (c) comparing said time lapses and, if the test time lapse is slower, adjusting the assembly condition of said test power assisted sliding door assembly.

5. The method as in claim 4 in which said secondary and primary positions are respectively characterized by a latch and striker being in general touching ajar relationship and in a locked secured relationship.

6. The method as in claim 5, in which said position are further characterized by additional door closure alignment elements which respectively are in a general touching ajar relationship and in a fully aligned secured relationship.

\* \* \* \* \*